United States Patent [19]

Fink

[11] Patent Number: 5,092,336
[45] Date of Patent: Mar. 3, 1992

[54] METHOD AND DEVICE FOR LOCALIZATION AND FOCUSING OF ACOUSTIC WAVES IN TISSUES

[75] Inventor: Mathias Fink, Meudon, France

[73] Assignee: Universite Paris VII-Bureau de la Valorisation et de Relations Industrielle, Paris, France

[21] Appl. No.: 476,682

[22] Filed: Feb. 8, 1990

[30] Foreign Application Priority Data

Feb. 8, 1989 [FR] France .................. 89 01628

[51] Int. Cl.⁵ .......................................... A61B 17/22
[52] U.S. Cl. .................. 128/660.03; 128/24 EL; 128/660.01
[58] Field of Search ............ 128/660.01, 660.03, 128/24 A, 24 EL; 73/599, 602; 606/127, 128; 367/95, 124–125

[56] References Cited

U.S. PATENT DOCUMENTS

| | | | |
|---|---|---|---|
| 4,315,514 | 2/1982 | Drewes et al. | 128/660.03 |
| 4,526,168 | 7/1985 | Hassler et al. | 128/303 |
| 4,757,820 | 7/1988 | Itoh | 128/660.03 |
| 4,865,042 | 9/1989 | Umemura et al. | 128/660.03 |

OTHER PUBLICATIONS

IEEE 1987 Ultrasonics Symposium Proceedings, Denver, Colorado, October 14–16, 1987, vol. 2, pp. 863–866, IEEE, New York, U.S.; M. Ibbini et al: "Ultrasound Phased Arrays for Hyperthermia: New Techniques Based on the Field Conjugation Method" p. 863, col. 1, line 44–p. 863, col. 2, line 6.

*Primary Examiner*—Francis Jaworski
*Attorney, Agent, or Firm*—Larson and Taylor

[57] ABSTRACT

For focussing an ultrasound beam delivered by a transducer array on a reflective target in a medium, for instance in organic tissues, the zone including the target is illuminated with an unfocussing acoustic beam. The shapes and position of echo signals delivered by electroacoustic transducers of a regular array are individually stored; the distribution in time and the shapes of the echo signals for obtaining reversed signals are reversed and the reversed signals are applied to the respective transdcuers of the array.

15 Claims, 3 Drawing Sheets

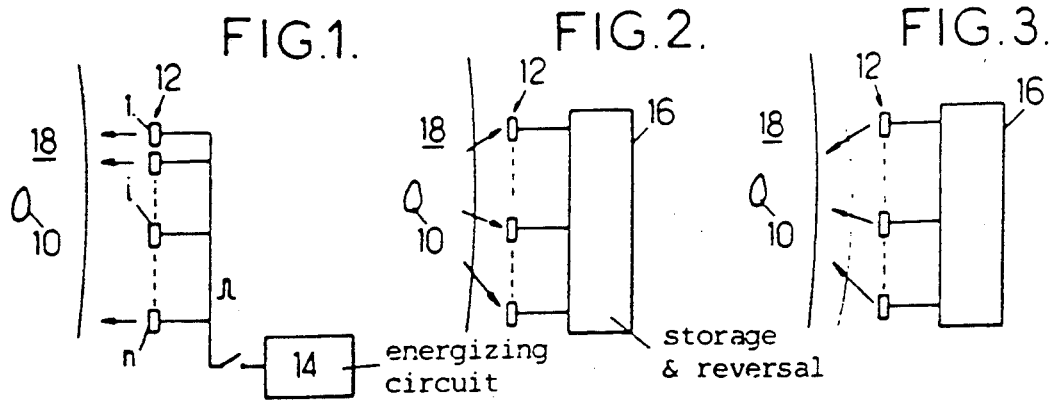
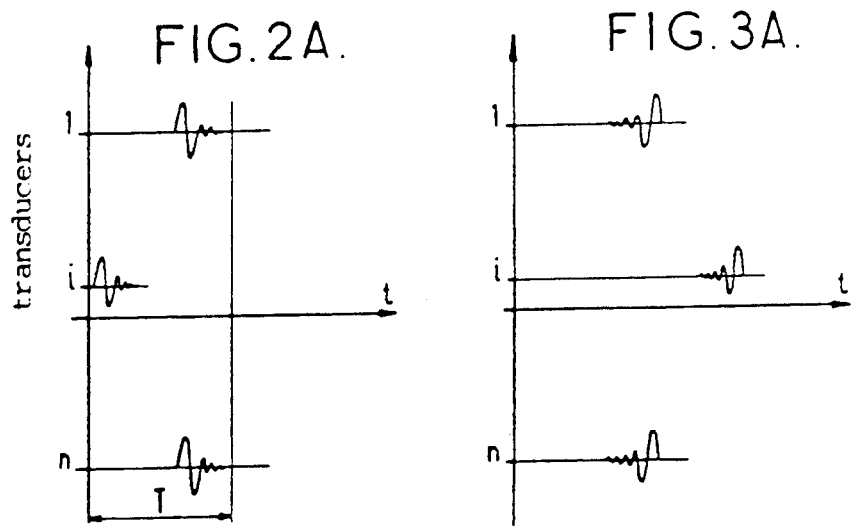
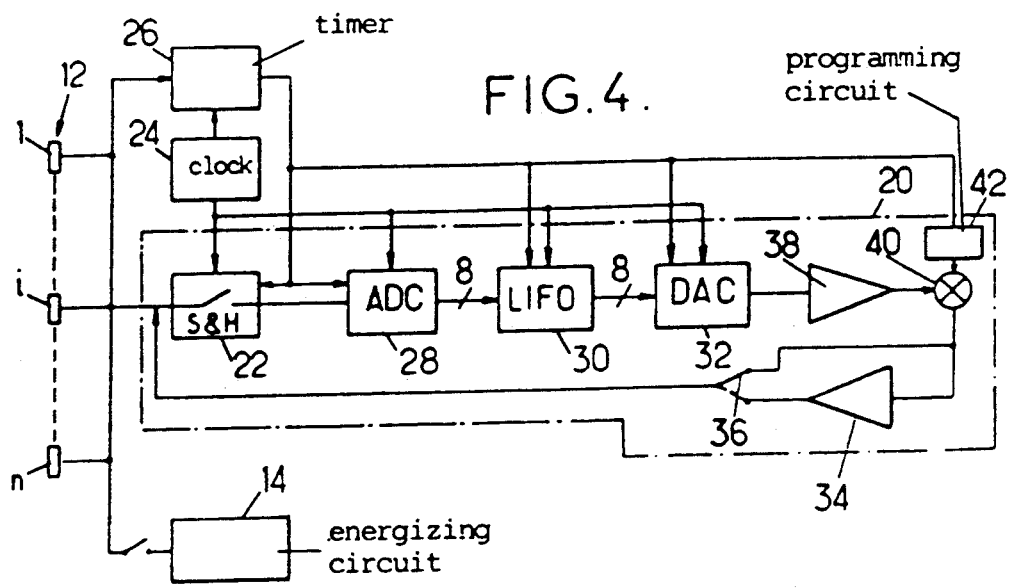

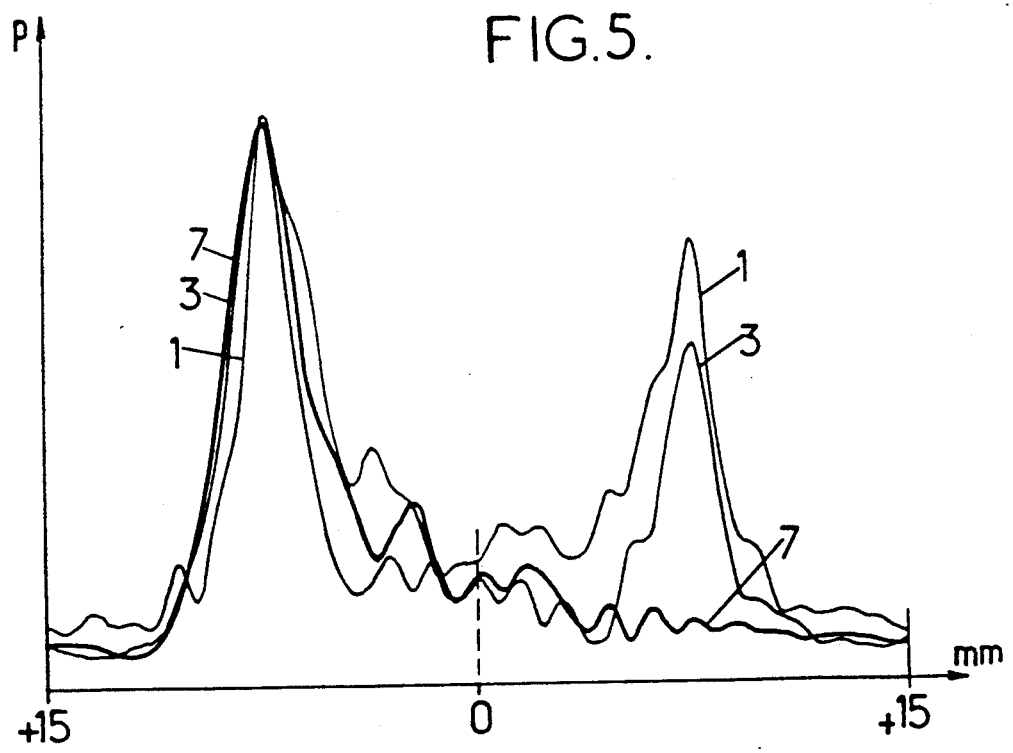

METHOD AND DEVICE FOR LOCALIZATION AND FOCUSING OF ACOUSTIC WAVES IN TISSUES

BACKGROUND OF THE INVENTION

1. Field of the Invention

The invention relates to a process and a device for localizing targets and focusing acoustic waves (the word "acoustic" being understood in a broad sense, without limitation of the audible frequency range) on targets which have an acoustic impedance significantly different from that of the environment. Such targets include solid objects in a sea environment or in sediments at the bottom of water bodies, cavities close to the earth surface. However, the invention is particularly suitable for use in localizing and possibly destructing calculi in human tissues, particularly the kidneys, the vesicle, the bladder and the urethra, as well as detection and localization of flaws, faults and heterogeneities in various materials, such as metals, composite materials and ceramics.

2. Prior Art

Lithotripty devices are already known comprising an ultrasonic generator whose transmitter is a rectangular or circular transducer array energized so as to generate an ultrasonic field focused on the assumed position of the calculus.

Due to the acoustic heterogeneity of the human tissues, knowledge of the geometrical position of a calculus, obtained for example by X-rays, is not sufficient to determine which time delays between pulses energizing the transducers or distribution in space of these transducers, will result in accurate focusing on the calculus. Beams must consequently be used whose focus spot is relatively wide, often about 1 cm². To obtain an energy density sufficient to destroy a calculus, powerful sources must be used which are cumbersome and expensive. And the lack of centering accuracy may damage tissues close to the calculus due to heating, all the more so since the calculus may have moved between the time of localizing it and the time of applying the destruction beam.

It might be thought that the problem can be overcome by using a lithotripty device which further comprises means for forming an echographic image by means of a transducer array (U.S. Pat. No. 4,526,168). But, in practice, the additional means do not solve the problem since applying energization pulses to the different transducers with the same distribution of delays as that which corresponds to focusing on a detected calculus does not concentrate the whole energy on the calulus, which has finite dimensions and a shape which may be irregular.

It is an object of the invention to provide a process and device for accurately focusing an ultrasonic beam on a target of high reflectivity, such as a calculus, and to provide self-adaptation of the wave front to the shape and position of the target itself, possibly for the purpose of destroying it, whatever the shape of an interface or of interfaces between the array of transducers providing the ultrasonic beam and the target.

For that, the invention uses a technique which may be termed "phase conjugation sound amplification" due to some analogy with phase conjugation mirrors used in optics. With this technique, starting from an incident ultrasonic wave which diverges from a target (a calculus reflecting a beam which it receives, for example) a convergent wave may be formed which follows exactly the opposite path, possible distortions being compensated for. For that, the divergent wave is received on an array of detectors, the signals received are reversed in time as regards both their shape and their time distribution (i.e. their laws of variation in time are reversed and their orders of occurence are reversed) and the signals thus reversed are applied to the array.

In most cases, the target will constitute a secondary source, which reflects or scatters a wave beam applied to it. The target may for instance consist of:

a stone reflecting a beam received from an array of illumination transducers, a small size tumor impregnated with a contrast agent (which renders it possible to carry out ultrasonic hyperthermia), a fault in a solid object, a small size cavity within the ground, close to the surface.

An initial illumination of the zone where the target is expected to be found will provide an indication on the boundaries of the latter, which has an acoustic impedance very different from that of the surrounding and which will appear as a secondary source.

Consequently, there is provided a process according to the invention, including the steps of:

(a) illuminating a zone including a target to be detected with an unfocused beam;

(b) individually storing the shapes and positions of echo signals delivered by the transducers of an array; and (c) reversing the distribution in time and the shapes of the signals for obtaining reversed signals and applying said reversed signal to the respective transducers.

Echoes which are originally quite low may be progressively amplified, by applying an amplification coefficient at each reversal.

Possibly some or all transducers of the array are used, rather than separate means, for illuminating the zone during step (a).

The process may use iteration, by repeating a sequence consisting of steps (b) and (c), after a first illumination of the zone concerned in which a target is sought, which has a reflectivity higher than the average reflectivity of the environment. Each time reversal of the echo enhances the ratio between the energy reflected by the target of high reflectivity and the energy reflected or scattered by local irregularities.

The final step of the process may consist of recording and/or displaying the final sound wave front. However, when the process of the invention is used for destructing stones in tissues, such destruction may be made by focusing ultrasound energy with the same array or with an other array which is better adapted to delivery of a high amount of energy. In both cases, the wave front of the destruction beam will reproduce the recorded and/or displayed wave front. Once the final wave front has been recorded, it will often be sufficient to use only the time distribution of the first maxima received in return by each of the transducers of the array after several iterations and to energize the destruction transducer array by simply respecting such time distribution, while disregarding the secondary lobes of the signal received and stored in digital form. Identification of the maximum of each signal and of its location in time raises no problem for well-known digital techniques exist for that purpose, using analog or digital correlators now commercially available. In some cases, it may however be advantageous to determine the time delay function to be respected, by evaluating the cross-correlations between a pair of signals.

Another solution consists in using, for destruction purpose, electronics which are distinct from the localization electronics but receive the information stored during localization, the same transducer array being used for localization and destruction.

During step (c) of the last sequence, an amplification gain is adopted such that destruction of the calculus is caused if such a purpose is to be obtained while the energy transmitted during localization may possibly be low.

It is important to note that the process which has just been described achieves a progressive selfadaptation of the wave form to the shape of the target; the distribution in time of the signals applied to the transducers and the shapes of the signals finally reflect exactly the shape of the calculus.

The process as hereinbefore described makes it possible to focus an ultrasound beam on the target which has a maximum reflectivity in an environment (or on a plurality of strongly reflecting targets if they are mutually spaced). Such focusing, when used for display purpose, "erases" the targets which have a lesser reflectivity and are masked by the target (or the targets) of maximum reflectivity. After a strongly reflecting target has been detected and localized, it may be useful to detect and localize targets which have a lesser reflectivity and which were masked by a main target during the initial focusing process. For that purpose, there is provided a process which includes, after a first focusing sequence as defined hereinabove, an additional sequence including the steps of:

(a1) illuminating the zone including the previously localized target with a non-focused wave beam;

(b1) collecting and storing echo signals received by the transducers of the array and individually storing the shapes and positions in time of said echo signals;

(b2) individually subtracting the echo signals received by each transducer of the array and stored during the last step (b) as defined above from the stored echo signals obtained during step (b1);

(c1) reversing the distribution time and the shapes of the results of the subtraction for obtaining further reversed signals and applying said further reversed signals to the respective transducers.

By repeating steps (b1) and (c1), the target whose reflectivity level is immediately lower than that of the target localized during the first sequence of operation may be detected and its position may be determined.

The above-defined process for detecting less reflective targets is simple but has a limitation: the final localization of the most reflecting target during the first sequence results from n transmission-reception sequences (n being an integer typically greater than 1) and the transfer function of the transducers modifies the echo signal upon each sequence. For removing the perturbating effect due to the accumulated distortions, step (b1) may include the additional phase consisting in subjecting the echo signals received by the transducers to n convolution operations, each corresponding to a transmission-reception sequence, before the echo signals representing the wave front on the most reflective object are subtracted.

Rather than carrying n convolution operations on the first reflected wave front, it is possible to carry out n deconvolution operations on the stored wave front.

The invention also provides a device for implementing the above-defined process, comprising: a transducer array; and, associated with each transducer of the array, a processing channel comprising an A/D converter, memory means, a programmable power transmitter controlled by the memory means, and means for energizing the transmitters in accordance with a time distribution which is reverse of the distribution stored in said memory means.

The device may be complemented with echography means for displaying the echo producing targets in the observation zone; targets on which the energy will subsequently be focused may be selected, for example by selecting some only of the transducers for later use.

Due to this arrangement, the energy applied to the transducers is used under much better conditions than in the past. In particular, if calculus is small of size, the focal spot may be reduced to the minimum allowed by diffraction and which, for an ultrasonic frequency of 1 MHz, is a few $mm^2$. It is not necessary that the transducers be accurately positioned in the array, for the time reversal accomodates possible positioning errors.

The invention will be better understood from the following description of particular embodiments, given by way of non-limitative examples.

BRIEF DESCRIPTION OF THE DRAWINGS

FIGS. 1, 2 and 3 are general diagrams showing three successive phases in the implementation of the process of the invention;

FIG. 2A and 3A are timing diagrams showing one example of electric signals respectively coming from the transducers (FIG. 2A) and applied to the transducers (FIG. 3A);

FIG. 4 is a general diagram of a channel associated with a transducer in a device in accordance with the invention;

FIG. 5 is a diagram wherein curves represent the distribution of pressure in the plane of the target at different phases of the process of the invention, respectively after the first, the third and the seventh iterations (curves designated by numerals 1, 3 and 7);

DETAILED DESCRIPTION OF PREFERRED EMBODIMENTS

Figure 7:
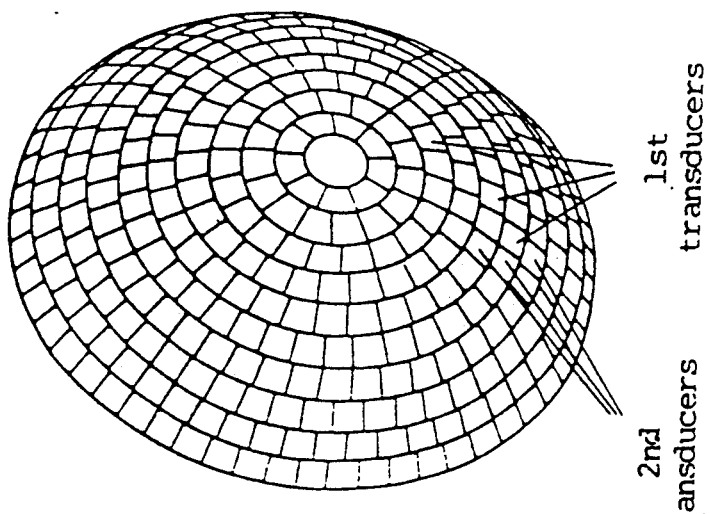
FIG. 7 is a schematic isometric view indicating a possible arrangement of transducers in an array for lithotripty.

As shown in FIGS. 1 to 3, implementation of the process of the invention requires forming, starting from a target constituting a secondary source 10, an ultrasonic pressure field focussed on the target, by an ultrasonic phase conjugation mirror technique.

The target may for instance be a stone to be destroyed in human tissues. It may also be a fault in a solid part.

During a first step, the zone in which a target 10 is to be localized is illuminated with a wide non-focused beam (FIG. 1). The beam may be supplied by an array 12 of ultrasonic transducers 1, 2, ..., i, ..., n which will again be used during the following steps. The transducers will generally be distributed in a two-dimensional array 12, although the Figures show the transducers distributed along a line, namely a one-dimensional array, for greater simplicity. The array may be flat or concave so as to provide geometric prefocusing when that is necessary for destroying the target by ultrasonic energy. The transducers may be of conventional construction and formed as piezo-electric ceramic wafers. It will often be advantageous to use transducers having a central resonance frequency of about 500 kHz for lithotripty. For medical use, the array may comprise transducers spaced apart by 3 to 6 wavelengths if placed on a concave surface, by 1 to 4 wavelengths in the case of a flat surface. The array may typically be designed to be placed at a distance from the calculus to be destroyed between 100 and 200 millimeters.

The array 12 may have one of the general constructions well known at the present time, so that it is not necessary to describe it further.

Array 12 is associated with a first circuit 14 for energizing the transducers by signals so shaped and distributed that the array delivers an unfocused beam directed toward the target 10 which, due to reflection from its surface, will constitute a secondary source. In practice, circuit 14 may be a generator of short pulses driving all the transducers in phase. A special array of transducers or some of the transducers may be used during this step instead of the complete array 12.

During a second step of the process, the echo received by the transducers $1, \ldots, i, \ldots, n$ is transformed into electric signals and the shapes and relative positions in time of the signals are stored by a circuit 16 (FIG. 2) which may have the construction which will be described with reference to FIG. 4. FIG. 2A shows the general shapes and time distribution of electric signals which may appear at the outputs of the different transducers when the electric signal energizing the transducers (FIG. 1) is a short pulse.

During the next step, the stored signals are used for generation of signals energizing the transducers of the reception array 12, after reversal of the distribution in time and of the shape of the signal (FIG. 3). To the extent that the transducers have a linear response and/or have the same response characteristic at emission and at reception, the returned wave front resulting from energization of the array 12 is focused on the target 10, the distortions appearing on the outgoing path through the possibly inhomogeneous medium 18 (FIG. 2) being exactly compensated for by the distortions on the return path. The divergent ultrasonic wave picked up by array 12 (FIG. 2) is used to generate an exactly focused convergent wave (FIG. 3).

To the extent that the target 10 is situated in a medium providing only much lower reflections, the third step which has just been described may be carried out with very high amplification of the signal, the amplification gain g between the electric signal delivered by the transducers and the electric signal which is applied thereto by circuit 16 possibly being as high as $10^5$ so as to provide the acoustic energy required for destroying the target when for example a calculus.

In some cases, a main calculus to be detected and possibly destroyed may be accompanied by smaller size stones which give rise to weaker echoes. So that the weaker echoes may be detected and selection by an operator can be made, circuit 16 may be associated with conventional display means of a type currently used in ultrasonic echography apparatus: then, on the B-scan image which is presented to him, an operator may select the wave front or the wave fronts which he wishes to reverse and amplify: for example, he may limit the time selection gate of circuit 16 by acting on the sequencer and possibly select different time gates or windows for different groups of transducers.

Selection by an operator may often be avoided by using an iteration process: after the first reversal, instead of transmitting a very amplified destruction convergent wave to the target, a new low-power echo is generated which is detected. Each repetition of the sequence, during a period which maybe termed "stand-by mode" or "waiting mode", the echoes of minor importance are progressively deleted and finally only the wave front on the target which has the highest reflectivity remains stored. After the stand-by mode, the last transmission from the transducers of array 12 may be very greatly amplified for destroying the target when required.

Circuit 16 may have the construction shown schematically on FIG. 4, in which a single channel, 20, associated with the transducer number i, is shown. Each channel may comprise a sample and hold circuit or sampler 22 for delivering analog samples of the signal received by transducer i, at the frequency of a clock 24 (3 to 10 MHz in general), during time intervals fixed by a timer 26 and having a sufficient duration T for the echo to be received by all transducers (FIG. 2A). The sampler 22 is followed by an A/D converter 28. Digitization over eight bits is generally sufficient to satisfactorily represent the dynamics of the echoes. The bytes each representative of a sample are stored in a LIFO memory 30 having a capacity sufficient for storing all samples received during the time T (FIG. 2A). Time reversal will be carried out on the signals received during time T only.

The timer 26 is arranged to cause sampling to begin after given time after energization of the transducers by generator 14; a proper time may easily be computed from knowledge of the velocity of ultrasounds in the propagation medium.

Timer 26 is also adapted to cause transmission of the reversed wave front after a predetermined short time $\tau$ has elapsed following the end of the last echo. It is in fact desirable for this time to be brief (a few milliseconds for example) so that neither the medium, nor the position of the target has changed between the outgoing and return.

For transmission of a reversed wave front, each channel 20 comprises a D/A converter followed by a high gain amplifier 34 which can be switched in or out by a switch 36 (which may be replaced by an amplifier gain control). The output of switch 36 drives the respective transducer i.

The number of successive sequences to be carried out may be set manually before initialization or each sequence may be triggered manually with switch means (not shown).

As illustrated in FIG. 4, each channel further comprises an amplifier 38 having a gain which is much lower than that of amplifier 34 and which is followed with an attenuator 40 whose function is to compensate for the absorption variations responsive to the depth of the target. The attenuation coefficient of attenuator 40 is modified in time by a programmer 42 which stores a function which is the reverse of the negative absorption exponential function in the medium between the transducer array and the target. The timer 26 is arranged for initialization of the programmer 42 which, as time elapses, decreases the amount of attenuation subjected by the signal output by amplifier 38.

It can be seen that, in a channel in which the instantaneous ultrasonic pressure field applied to the transducer is of the form p(x,y,t), the contribution of the transducer to the ultrasonic pressure field applied to the calculus 10 will be of the form p(x,y,τ−t). τ designates an arbitrary predetermined instant, which is later than the end of the observation time range.

As was mentioned above, the steps illustrated in FIGS. 2 and 3 may be repeated several times before the final high amplification step. It is important to note that the operation is iterative at all stages: the first "firing" (FIG. 1) roughly illuminates the zone of interest and makes it possible to detect the presence of any target with higher reflectivity than the mean reflectivity of the environment. A first time reversal (FIGS. 2 and 3) of the echoes enhances the energy applied to the high reflectivity target and the reversed beam illuminates preferably this part. If there are successive iterations, self-adaptation of the beam occurs, all the more rapidly the higher the ratio between the reflectivity of the target and the mean reflectivity of the environment. The wave front is finally adjusted exactly to the discontinuity represented by the boundary of the target. If the target moves during the successive sequences, time reversal adapts the pressure field to the new actual position of the object, i.e. provides echo tracking.

Numerous modifications of the invention are possible. In particular, it is possible to use analog rather than and not digital channels. Then, the input A/D converter, the LIFO (generally a RAM) and the output D/A converter are replaced by an analog circuit capable of storing the wave received in analog form and of delivering it in reversed form. At the present time, surface wave solid state components are known which permit such storage and reversal. Each component may in particular be formed on a silicon substrate carrying a first surface wave component intended for storage, a multiplier for modulation by a high frequency wave and a second surface wave component for retrieval.

The process and device which have just been described can be used not only when a final step is provided for destruction, by concentration of ultrasonic energy, but also when only localization is required, destruction being possibly carried out subsequently with the same or other means.

The favorable results provided by the invention will be more apparent from a consideration of the following example. Thirty-two transmitter-receiver transducers were distributed as a linear array on a cylindrical sector having an axis parallel to two wires, one of which having a diameter double of that of the other. The distance between the transducers and the midline between the two wires was 18 mm. Tests were made with the transducers and wires immersed in a liquid. Energy distribution in the common plane of the two wires was measured, for each "firing", with a hydrophone moved in the common plane of the two wires and responsive to the ultrasound pressure p.

Referring to FIG. 5, where the acoustic pressure p is in ordinates and plotted against time, after a first sequence (i.e. at the first transmission after time reversal), the energy directed toward the wire of greater diameter is greater than toward the wire of lesser diameter. The difference between the amounts of energy is increased after the third sequence (curve 3) at the seventh sequence, the major part of the energy is concentrated on the wire of larger diameter and the other wire does not appear any longer on the curve.

Figure 6B:
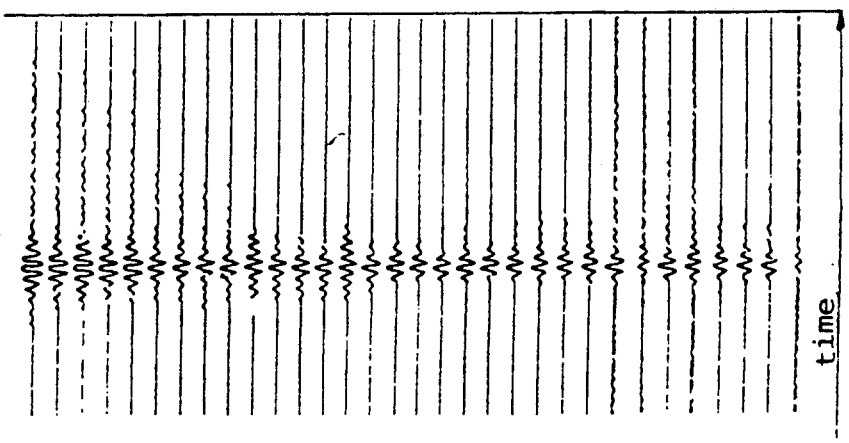
FIGS. 6A and 6B are time diagrams which respectively show the echo signals delivered by the transducers of a cylindrical array at receipt of the first echo on the target and the contribution of the transducer to the acoustic pressure field applied to the target after the first reversal.
Figure 6A:
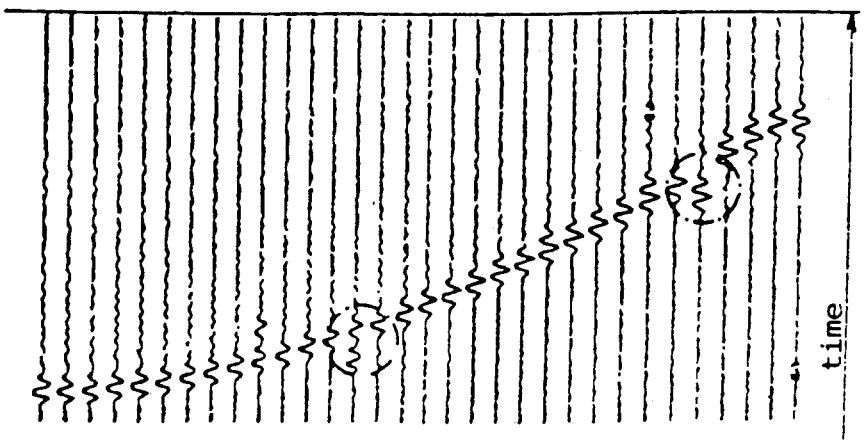

A similar test made with a linear array of transducers, some of which have defects, has proven that the favorable results are retained, which constitutes a supplemental advantage of the invention. Referring to FIG. 6A, the time distribution and the shape of the echo signals returned to the transducers of an array similar to that of the preceding example are shown. Two of the transducers deliver signals which have defects. They are indicated with circles in dash-dot lines. The time reversal corrects the defects of the transducer array. Referring to FIG. 6B, which illustrates the acoustic pressure signal delivered by a hydrophone moved in a plane orthogonal to the midplane of the array, the defects appearing on FIG. 6A are eliminated and the signals reaching the target are in phase.

As indicated above, the transducers may be distributed at the nodal points of arrays of quite different types. Referring to FIG. 7, an array comprises more than 100 transducers distributed along concentric circles, on a spherical cap. Localization by successive time reversals is preferably carried out with some only of the transducers which are evenly distributed in the array. For instance, only one transducer among m (with m typically equal to 5) is used. The transducers used for localization are provided with a full channel as illustrated in FIG. 4. The additional transducers, which are not used for localization but only for destruction of the target, are energized during the final step only. The time at which they are energized and possibly the shape of the signals applied to them are computed by interpolation between the signals stored for the adjacent transducers used for localization. Consequently, the additional transducers are connected to the output of a simplified channel including only at interpolator receiving input signals from the output of the digital/analog converters 32 of the channels 20 associated with adjacent transducers and a power amplifier. Manually actuated switch means may be used for enabling energization of the additional transducers when needed.

I claim:

1. A process for acoustically localizing a reflective target in an environment, comprising the steps of:
   (a) illuminating a zone of the environment including a target to be detected with an unfocussed acoustic beam;
   (b) individually storing the shapes and positions of echo signals each delivered by one of a plurality of electro-acoustic transducers distributed at nodal points of a geometrical array following illumination by said acoustic beam;
   (c) reversing the distribution in time and the shapes of each of the echo signals for obtaining reversed signals; and
   (d) applying each of said reversed signals to the transducer of the array from which the respective reversed signal was derived for illuminating said zone again.

2. Process according to claim 1, including illuminating said zone with at least some of said transducers of the array during step (a).

3. Process according to claim 1, including repeating a sequence constiting of steps (b), (c) and (c) several times and amplifying the echo signals each time they are reversed.

4. Process according to claim 3, further including the step of storing the time distribution of said echo signals at the end of a last step (c).

5. Process according to claim 4, including determining said time distribution by a cross-correlation process.

6. Process according to claim 3, further including storing the time distribution of maximum values of said echo signals at the end of last step (c).

7. Process for localizing an object which has a reflectivity lower than that of a target but higher than that of the balance of the environment, comprising the steps of:
  (a) illuminating a zone of the environment including said target and said object with an unfocussed acoustic beam;
  (b) individually storing the shapes and positions of echo signals each delivered by one of a plurality of electro-acoustic transducers distributed at nodal points of a geometrical array following illumination by said acoustic beam;
  (c) reversing the distribution in time and the shapes of each of the echo signals for obtaining reversed signals;
  (d) applying each of said reversed signals to the transducer of the array from which the respective reversed signal was derived for illuminating said zone again;
  (a1) illuminating said zone including the previously localized target with a non-focussed acoustic wave beam;
  (b1) collecting and storing echo signals received by the transducers of said array and individually storing the shapes and positions in time of said echo signals;
  (b2) individually subtracting the echo signals received by each transducer of the array and stored during said last step (b) from the stored echo signals obtained during step (b1);
  (c1) reversing the time distribution and the shapes of the results of the subtraction for obtaining further reversed signals; and
  (d1) applying said further reversed signals to the respective transducers of said array.

8. Process according to claim 7, further including subjecting the echo signals received by the transducers during step (b1) to n convolution operations, each corresponding to a transmission-reception sequence, before the echo signals representing the wave front on the target are subtracted, n being the number of sequences of steps (b) and (c).

9. A device for acoustic processing of acoustic wave reflective targets in an environment, comprising:
  means for illuminating a zone of the environment including said targets with an unfocussed acoustic beam;
  plurality of electro-acoustic transducers distributed in an array; and
  a respective processing channel associated with each of said transducers and having:
    means for storing the wave form and time occurence of an echo signal received by the respective transducer and for generating a wave whose shape and time occurence are reverse; and
    means for amplifying the reversed wave and applying it to the respective transducer.

10. A device according to claim 9, wherein said array further comprises, in addition to said transducers which are evenly distributed at only some of the nodal points of said array and which are each connected to a respective one of said processing channels, a plurality of additional transducers located at the remaining nodal points of said array and wherein an input of each of said additional transducers is connected to means for applying to the respective additional transducer a signal whose time occurrence is computed by interpolation between time occurrences of the signals applied to adjacent ones of said transducers which are connected to respective ones of the processing channels.

11. A device according to claim 9, further comprising echography means for displaying all possible targets in said environments and means for selecting some only of said transducers for focusing energy on a selected one of said targets.

12. A device for acoustic localization of acoustic wave reflective targets in an environment, comprising:
  means for illuminating a zone of the environment including said targets with an unfocussed acoustic beam;
  a plurality of electro-acoustic transducers distributed in an array; and
  a respective processing channel associated with each of said transducers and having:
    means for storing the wave form and time occurence of an echo signal received by the respective transducer and for generating a wave whose shape and time occurence are reversed; and
    means for amplifying the reversed wave and applying it to the respective transducers.

13. A process for destructing a stone in tissues with focussed ultra-sound energy, comprising the steps of:
  (a) illuminating a zone of the environment including a target to be detected with an unfocussed acoustic beam;
  (b) individually storing the shapes and positions of echo signals each delivered by one of a plurality of electro-acoustic transducers distributed at nodal points of a geometrical array following illumination by said acoustic acoustic beam;
  (c) reversing the distribution in time and the shapes of each of the echo signals for obtaining reversed signals;
  (d) applying each of said reversed signals to the transducer of the array from which the respective reversed signal was derived for illuminating said zone again;
  (e) individually storing at least the relative time positions of maxima of the echo signals each delivered by one of said electro-acoustic transducers,
  whereby the ratio between the energy reflected by the target and the energy reflected or scattered by local irregularities in said tissues is enhanced and a final ultra-sound wave front can be recorded; and
  reproducing said wave front with an increased amount of ultra-sound energy for focussing sufficient ultra-sound energy on said stone to destruct said stone.

14. Process according to claim 13, wherein said ultra-sound energy for destruction is focussed with at least some of the transducer of said array.

15. Process according to claim 13, wherein only the time distribution of the first maxima received by each of the transducer of the array after a plurality of iterations is stored and the transducer array is energized by respecting such time distribution for destruction.

* * * * *